United States Patent [19]

Revis

[11] Patent Number: 4,754,046

[45] Date of Patent: Jun. 28, 1988

[54] STABILIZED SILYL KETENE ACETALS

[75] Inventor: Anthony Revis, Freeland, Mich.

[73] Assignee: Dow Corning Corporation, Midland, Mich.

[21] Appl. No.: 66,809

[22] Filed: Jun. 25, 1987

[51] Int. Cl.$^4$ .............................. C07F 7/08; C07F 7/10; C07F 7/18
[52] U.S. Cl. .................................................... 556/401
[58] Field of Search ........................................ 556/401

[56] References Cited

U.S. PATENT DOCUMENTS

| | | | |
|---|---|---|---|
| 4,414,372 | 11/1983 | Farnham et al. | 526/190 |
| 4,417,034 | 11/1983 | Webster | 526/190 |
| 4,508,880 | 4/1985 | Webster | 526/190 |
| 4,683,319 | 7/1987 | Yoshitake et al. | 556/401 X |

OTHER PUBLICATIONS

*Chemical and Process Technology Encyclopedia* (1974), pp. 131–135.
Petrov et al., *J. Gen. Chem. (USSR)*, 29(1959), pp. 2896–2899.
Rutbottom and Marreno, *Syn. Comm.* 11(6) (1981), pp. 505–511.
Tamao and Maeda, *Tetrahedron Letter*, 27:1 (1986), pp. 65–68.

*Primary Examiner*—Paul F. Shaver
*Attorney, Agent, or Firm*—Carl A. Yorimoto

[57] ABSTRACT

There is provided a silyl ketene acetal mixture which has a reduced susceptibility to oxidation on exposure to ambient air. The silyl ketene acetal mixture comprises a silyl ketene acetal to which is added a phenolic compound, the phenolic compound being present in an amount sufficient to be effective as an oxidation inhibitor.

24 Claims, No Drawings

STABILIZED SILYL KETENE ACETALS

BACKGROUND OF THE INVENTION

This invention relates to silyl ketene acetals which are stabilized against oxidation with ambient oxygen. More specifically, this invention relates to silyl ketene acetals in which a minor portion of a phenolic compound has been added as an oxidation inhibitor.

The first reference to preparation of silyl ketene acetals (SKA) was in the late-1950's by Petrov et al., *J. Gen. Chem.* (USSR), 29(1959), pp. 2896-2899. Silyl ketene acetals are characterized by the backbone structure,

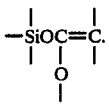

These organosilane intermediates are of interest because of the ability to further react the SKA's to other intermediates which would be difficult to synthesize by other means. A very recent application is the use of SKA's as acrylate polymerization initiators. This concept known as Group Transfer Polymerization (GTP) was developed by DuPont and is disclosed in three recent U.S. patents—U.S. Pat. No. 4,414,372, Farnham et al., issued Nov. 8, 1983; U.S. Pat. No. 4,417,034, Webster, issued Nov. 22, 1983; and U.S. Pat. No. 4,508,880, Webster, issued Apr. 2, 1985.

Rutbottom and Marreno, *Syn. Comm.*, 11(6) (1981), pg. 505-511, discloses that meta-chloroperbenzoic acid (MCPBA) oxidizes SKA's to form alpha-hydroxy esters. Tamao and Maeda, *Tetrahedron Letter,* 27: 1 (1986), pp. 65-68, report that vinyl alkoxysilanes undergo a similar oxidative rearrangement with MCPBA.

Phenolic compounds, primarily phenolic compounds with a hindered structure, are known to be polymerization inhibitors for vinylic materials such as acrylates and methacrylates. Inhibitors such as 4-methoxyphenol, 2,6-di-t-butyl-4-methylphenol, and 2,4-di-methyl-6-t-butylphenol are known to be effective in preventing radical chain polymerization of alpha,beta-unsaturated esters. 2,4-di-methyl-6-t-butylphenol, also known as butylated hydroxytoluene or BHT, is also known as an antioxidant for food, animal and vegetable oils, synthetic rubber, plastics, and soaps.

None of the above references demonstrate or suggest the mixture of an SKA and a phenolic compound as disclosed by the instant invention.

The objective of the instant invention is to provide a silyl ketene material with a significantly reduced susceptibility toward oxidation on contact with ambient air.

DESCRIPTION OF THE INVENTION

In accordance with the instant invention there is provided a silyl ketene acetal mixture which has a reduced susceptibility to oxidation on exposure to ambient air, the composition of this mixture being described herein. What is described therefore, is a silyl ketene acetal mixture, said silyl ketene acetal having reduced susceptibility to oxidation, said mixture comprising (A) a silyl ketene acetal, the silyl ketene acetal being present as a major portion; and (B) a phenolic compound, said phenolic compound being present as a minor portion and being present in an amount sufficient to be effective as an oxidation inhibitor.

Generically, a silyl ketene acetal is a compound with the structural backbone,

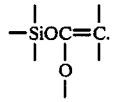

Any SKA can be stabilized in this invention. Substituent groups of the SKA are not critical to the invention so long as these groups are not reactive with the phenolic compound. Preferred silyl ketene acetals may be selected from a group consisting of

 (A)

 (B)

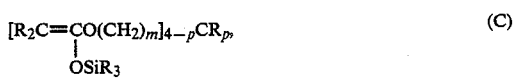 (C)

wherein
each R is independently selected from a group consisting of alkyl groups containing 1 to 4 carbon atoms, alkoxy groups containing 1 to 4 carbon atoms, aryl groups, and alkaryl groups; wherein a is 0, 1, 2, or 3; n is 0, 1, 2, 3, 4, 5, or 6; m is 0, 1, 2, 3, 4, 5, or 6; and p is 0, 1, 2, or 3;
wherein Z is selected from a group consisting of

 (i)

wherein Y is selected from a group consisting of $C_{1-20}$ alkyl, alkenyl, or alkadienyl; $C_{6-20}$ cycloalkyl, aryl, alkaryl, or aralkyl; any of said group containing one or more ether oxygen atoms, tertiary amino groups, amido groups, thio groups, siloxy groups, or carbonyl groups within aliphatic segments thereof; and any of such group containing one or more functional substituents that are unreactive under silylating conditions,

 (ii)

wherein W is selected from a group consisting of $C_{1-20}$ alkyl, alkenyl, or alkadienyl; $C_{6-20}$ cycloalkyl, aryl, alkaryl, or aralkyl; any of said group being terminated by trialkylsilyl groups, tertiary amino groups, isocyanato groups, perhalo groups, amido groups, thio groups, cyano groups, phosphonate groups, siloxy groups, or carbonyl groups thereof; and any of such group containing one or more functional substituents that are unreactive under silylating conditions,

 (iii)

wherein each $R^i$ is independently selected from the group consisting of alkyl radicals containing 1 to 4 carbon atoms, alkoxy groups containing 1 to 4 carbon atoms, and aryl groups,

 (iv)

wherein $G^1$ and $G^2$ are independently selected from the group consisting of (a) alkyl radicals containing 1 to 4 carbon atoms, aryl groups, and alkoxy groups containing 1 to 4 carbon atoms, (b) trialkylsilyl, and (c) alkyltrialkylsilyloxy;

wherein Q is selected from a group consisting of $C_{1-20}$ alkylene, alkenylene, or alkadienylene; $C_{6-20}$ cycloalkylene, arylene, alkarylene, or aralkylene; any of said group containing one or more ether oxygen atoms, tertiary amino groups, amido groups, thio groups, siloxy groups, or carbonyl groups within aliphatic segments thereof; and any of such group containing one or more functional substituents that are unreactive under silylating conditions; Silyl ketene acetals of the formula,

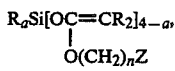

may be such materials as

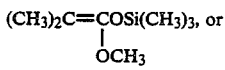

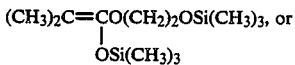

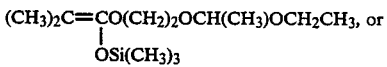

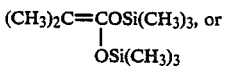

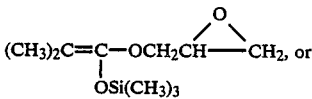

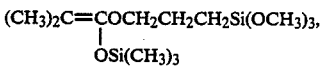

or like materials.

The inventor has unexpectedly found that silyl ketene acetals undergo auto-oxidation on exposure to ambient air to form alpha-siloxy ester of the general structure,

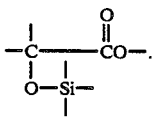

This oxidation was found to occur very rapidly, consuming as much as 5 weight percent of the desired SKA in one day. In the application of SKA's as an acrylate polymerization initiator, described supra, the presence of these alpha-siloxy esters severely compromises the purity of the SKA's and their effectiveness as polymerization initiators.

The phenolic compound can be represented by the general formula,

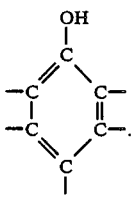

The phenolic compound can be selected from a group consisting of phenol and substituted phenols. The substituted phenols can be such materials as hydroquinone, 4-methoxyphenol, 2,6-di-t-butyl-4-methylphenol, 2,2'-methylene-bis-(6-t-butyl-p-cresol), 2,2'-thiobis-(6-t-butyl-p-cresol), 1,1,3-tris(2-methyl-4-hydroxy-5-t-butylphenylbutane), tetrakis(methylene(3,5-di-t-butyl-4-hydroxy cinnamate))methane, and like materials. These phenolic compounds are available commercially. Many of these substituted phenols are listed in *Chemical and Process Technology Encyclopedia* (1974), pp. 131-135.

For the purposes of the instant invention, the term "in an amount sufficient to be effective as an oxidation inhibitor" means that amount of the phenolic compound that will inhibit the oxidation of a silyl ketene acetal so that the initial siloxy ester concentration is not increased more than four-fold upon storage of 30 days in contact with ambient air or that the absolute content of the siloxy ester of the desired silyl ketene acetal is a maximum of about 10 weight percent. The substituted phenols are somewhat more effective as an oxidation inhibitor for SKA's than is phenol. The substituted phenols are a more preferred oxidation inhibitor than phenol. For the substituted phenols, alone, the term "in an amount sufficient to be effective as an oxidation inhibitor" means that amount of a substituted phenol that will inhibit the oxidation of a silyl ketene acetal so that the siloxy ester concentration is not increased more than about 50 to 75 percent upon extended storage of 20 days. Preferred phenolic compounds are selected from a group consisting of hydroquinone, 4-methoxyphenol, and 2,6-di-t-butyl-4-methylphenol.

It has been found in the instant invention that a molar concentration of a phenolic compound, relative to the SKA, of greater than about 100 parts per million is effective in inhibiting the formation of the undesirable siloxy ester. The inventor of the instant invention believes that inhibitor concentrations of less than 100 ppm can be effective, however, with less assurance of reliability. A preferred concentration of oxidation inhibitor is 500 ppm on a molar basis relative to the silyl ketene acetal. Higher concentrations of inhibitors are effective, however the inventor believes that concentrations of greater than 10,000 parts per million are not economically practical.

The following examples are presented to aid in the understanding of the instant invention by those skilled in the art. These examples are to be illustrative and are not to be construed as limiting the instant invention as delineated in the claims.

EXAMPLE 1

(Not within the scope of the instant invention)

A freshly distilled sample of a silyl ketene acetal (SKA) was exposed to ambient air to study the effect upon product quality. The SKA evaluated was

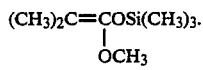

A stock mixture or master batch of material was made from the SKA and treated toluene. The toluene was added at about 3.5 weight percent to serve as an internal standard for subsequent gas chromatographic analyses. The toluene was treated by being distilled from calcium hydride. The toluene so treated was then stored over molecular sieves.

Approximately 1 gram (g) of the SKA was placed in a 8 milliliter glass vial. The vials were sealed with an appropriate cap. This volume of SKA left an air space above the liquid of approximately 80 percent of the volume of the vial. A sample of the freshly distilled SKA was analyzed, and will be designated as Sample A. Six other samples were prepared in the above manner, and these samples are designated as Samples B, C, D, E, F, and G. These samples were stored sealed under ambient conditions. The samples were held for various periods of time, and analyzed by gas chromatographic analysis. The most significant change noted in product quality was the formation of the siloxy ester species,

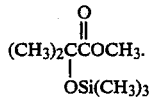

The starting SKA had a purity of 98.7 weight percent by gas chromatographic analysis. Table 1 is a summary of the results of analysis of the samples taken at various times. The analysis of the siloxy ester species, above, are reported in weight percent, designated as "%SiO". Time of sampling is reported in hours and days, and is designated "Time".

TABLE 1

| Sample | Time | % SiO |
|---|---|---|
| A | 0 hours | 0.26 |
| B | 0.5 | 0.50 |
| C | 1 | 0.64 |
| D | 3 | 1.24 |
| E | 5 | 2.39 |
| F | 24 | 4.56 |
| G | 4 days | 2.73 |
| C | 25 | 1.97 |
| E | 25 | 4.21 |

These above results demonstrate that silyl ketene acetals will oxidize upon contact with ambient air in the vapor space in a liquid storage vessel.

EXAMPLE 2

A study was made to evaluate the effect of the addition of a phenolic material as an inhibitor to the formation of the siloxy ester material shown to be generated upon exposure to ambient air in Example 1. Experimental and analytical procedures similar to those utilized in Example 1 were applied to this study.

The silyl ketene acetal was the same species as utilized in Example 1. This SKA had analysis of 97.6 weight percent SKA, as determined by gas chromatographic analysis. The stock SKA solution had an analysis of 94.8 percent SKA, 2.8 percent toluene, and 0.60 percent siloxy ester, all in weight percent. This stock solution was designated as Sample H.

The phenolic material evaluated was 2,6-di-t-butyl-4-methylphenol, hereafter referred to as BHT. Several samples were prepared by mixing BHT with the SKA stock solution at concentrations of approximately 6700, 3300, 1600, 750, and 130 parts per million, respectively, on a molar basis relative to the SKA. These samples are designated as Samples I, J, K, L, and M, respectively. The various samples were analyzed by a gas chromatographic technique at various times after being placed into the glass vials in contact with ambient air.

Table 2 is a summary of the results. The various samples are identified by content of BHT, expressed as parts per million (ppm) relative to the SKA, and designated as "ppm BHT"; by weight percent siloxy ester content, designated as "%SiO"; and by the time after addition of samples to the glass vials, expressed in days, designated "Time".

TABLE 2

| Sample | Time | ppm BHT | % SiO |
|---|---|---|---|
| H | 0 | 0 | 0.60 |
| I | 3 | 6700 | 0.42 |
| J | 3 | 3300 | 0.41 |
| K | 3 | 1600 | 0.33 |
| L | 3 | 750 | 0.43 |
| M | 3 | 130 | 0.43 |
| H | 3 | 0 | 0.83 |
| H | 24 | 0 | 3.56 |
| M | 24 | 130 | 0.69 |

These above results demonstrate that 2,6-di-t-butyl-4-methylphenol is an effective inhibitor to the oxidation of a silyl ketene acetal.

EXAMPLE 3

A study was undertaken to evaluate the effectiveness of several phenolic compounds as oxidation inhibitors for the silyl ketene acetal,

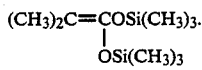

The phenolic compounds evaluated were phenol, 4-methoxyphenol (MEHQ), and hydroquinone (HQ).

The experimental and analytical procedures are similar to those utilized in Examples 1 and 2. The stock solution of this SKA in toluene had an analysis by gas chromatographic analysis of 86.9 weight percent SKA, 8.2 percent toluene, and 2.7 percent siloxy ester. Table 3 is a summary of the various samples, mixed with above inhibitors and analyzed after various times of exposure to ambient air in a sealed state. The stock SKA solution in toluene is designated as Sample N. The remaining samples are designated as Samples O, P, Q, R, S, and T, respectively. The results in Table 3 are reported by inhibitor used, designated as "Inhib"; concentration of inhibitor in SKA in ppm on a molar basis, designated as "ppm"; time in hours after exposure to ambient air, designated as "Time"; and siloxy ester content of the SKA solution in weight percent, designated as "%SiO".

TABLE 3

| Sample | Inhib | ppm | Time | % SiO |
|--------|-------|-----|------|-------|
| N | None | 0 | 0 | 2.7 |
| N | None | 0 | 24 | 19.6 |
| N | None | 0 | 68 | 34.2 |
| O | Phenol | 180 | 24 | 3.7 |
| O | Phenol | 180 | 67 | 5.3 |
| P | Phenol | 360 | 24 | 4.9 |
| P | Phenol | 360 | 67 | 8.6 |
| Q | MEHQ | 160 | 24 | 2.3 |
| Q | MEHQ | 160 | 67 | 2.5 |
| R | MEHQ | 310 | 24 | 2.4 |
| R | MEHQ | 310 | 65 | 2.5 |
| S | HQ | 150 | 24 | 2.3 |
| S | HQ | 150 | 65 | 2.5 |
| T | HQ | 300 | 24 | 2.1 |
| T | HQ | 300 | 65 | 2.5 |

These above results demonstrate the oxidation inhibiting effect of phenolic compounds mixed with silyl ketene acetals when exposed to ambient air in a sealed situation.

EXAMPLE 4

Another test was performed with the SKA species of Example 3, and 2,6-di-t-butyl-4-methylphenol (BHT).

The stock solution of the SKA in toluene had an analysis by gas chromatography of 87.0 weight percent SKA, 7.3 percent toluene, and 2.2 percent siloxy ester. Two samples were evaluated, the first with no BHT, the second sample with 170 ppm BHT. These samples are designated as Samples U and V, respectively.

Table 4 is a summary of the results. The samples are identified by content of BHT, expressed as parts per million (ppm) relative to the SKA, and designated as "ppm BHT"; by weight percent siloxy ester content, designated as "%SiO"; and by the time after addition of samples to the glass vials, expressed in hours and days, designated "Time".

TABLE 4

| Sample | Time | ppm BHT | % SiO |
|--------|------|---------|-------|
| U | 0 hours | 0 | 2.2 |
| U | 1 | 0 | 2.7 |
| U | 16 | 0 | 7.0 |
| U | 25 | 0 | 8.3 |
| V | 0 hours | 170 | 2.2 |
| V | 24 | 170 | 2.1 |
| V | 25 days | 170 | 2.1 |

These above results further demonstrate the oxidation inhibiting effect of phenolic compounds mixed with silyl ketene acetals when exposed to ambient air in a sealed situation.

What is claimed is:

1. A silyl ketene acetal mixture, said silyl ketene acetal having reduced susceptibility to oxidation, said mixture comprising
   (A) a silyl ketene acetal, the silyl ketene acetal being present as a major portion; and
   (B) a phenolic compound, said phenolic compound being present as a minor portion and being present in an amount sufficient to be effective as an oxidation inhibitor.

2. A silyl ketene acetal mixture according to claim 1, wherein the silyl ketene acetal is selected from a group consisting of

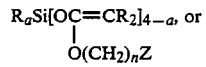  (A)

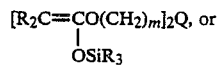  (B)

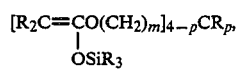  (C)

wherein
  each R is independently selected from a group consisting of alkyl groups containing 1 to 4 carbon atoms, alkoxy groups containing 1 to 4 carbon atoms, aryl groups, and alkaryl groups; wherein a is 0, 1, 2, or 3; n is 0, 1, 2, 3, 4, 5, or 6; m is 0, 1, 2, 3, 4, 5, or 6; and p is 0, 1, 2, or 3;
  wherein Z is selected from a group consisting of —Y,  (i)

wherein Y is selected from a group consisting of $C_{1-20}$ alkyl, alkenyl, or alkadienyl; $C_{6-20}$ cycloalkyl, aryl, alkaryl, or aralkyl; any of said group containing one or more ether oxygen atoms, tertiary amino groups, amido groups, thio groups, siloxy groups, or carbonyl groups within aliphatic segments thereof; and any of such group containing one or more functional substituents that are unreactive under silylating conditions,
  —W,  (ii)

wherein W is selected from a group consisting of $C_{1-20}$ alkyl, alkenyl, or alkadienyl; $C_{6-20}$ cycloalkyl, aryl, alkaryl, or aralkyl; any of said group being terminated by trialkylsilyl groups, tertiary amino groups, isocyanato groups, perhalo groups, amido groups, thio groups, cyano groups, phosphonate groups, siloxy groups, or carbonyl groups thereof; and any of such group containing one or more functional substituents that are unreactive under silylating conditions,
  —$SiR'_3$,  (iii)

wherein each $R^i$ is independently selected from the group consisting of alkyl radicals containing 1 to 4 carbon atoms, alkoxy groups containing 1 to 4 carbon atoms, and aryl groups,

  (iv)

wherein $G^1$ and $G^2$ are independently selected from the group consisting of (a) alkyl radicals containing 1 to 4 carbon atoms, aryl groups, and alkoxy groups containing 1 to 4 carbon atoms, (b) trialkylsilyl, and (c) alkyltrialkylsilyloxy;
  wherein Q is selected from a group consisting of $C_{1-20}$ alkylene, alkenylene, or alkadienylene; $C_{6-20}$ cycloalkylene, arylene, alkarylene, or aralkylene; any of said group containing one or more ether oxygen atoms, tertiary amino groups, amido groups, thio groups, siloxy groups, or carbonyl groups within aliphatic segments thereof; and any of such group containing one or more functional substituents that are unreactive under silylating conditions.

3. A silyl ketene acetal mixture according to claim 2, wherein the silyl ketene acetal has the formula,

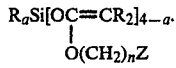

4. A silyl ketene acetal mixture according to claim 2, wherein the silyl ketene acetal has the formula,

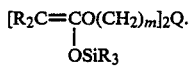

5. A silyl ketene acetal mixture according to claim 2, wherein the silyl ketene acetal has the formula,

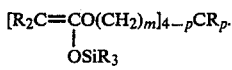

6. A silyl ketene acetal mixture according to claim 3, wherein the silyl ketene acetal is

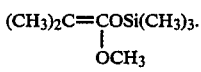

7. A silyl ketene acetal mixture according to claim 3, wherein the silyl ketene acetal is

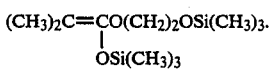

8. A silyl ketene acetal mixture according to claim 3, wherein the silyl ketene acetal is

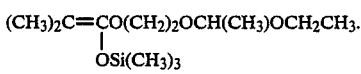

9. A silyl ketene acetal mixture according to claim 3, wherein the silyl ketene acetal is

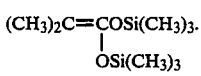

10. A silyl ketene acetal mixture according to claim 3, wherein the silyl ketene acetal is

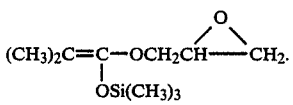

11. A silyl ketene acetal mixture according to claim 3, wherein the silyl ketene acetal is

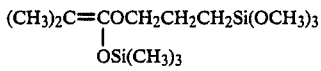

12. A silyl ketene acetal mixture according to claim 1, wherein the phenolic compound is selected from a group consisting of phenol and substituted phenols.

13. A silyl ketene acetal mixture according to claim 12, wherein the phenolic compound is a substituted phenol.

14. A silyl ketene acetal mixture according to claim 13, wherein the substituted phenol is selected from a group consisting of hydroquinone, 4-methoxyphenol, and 2,6-di-t-butyl-4-methylphenol.

15. A silyl ketene acetal mixture according to claim 1, wherein the silyl ketene acetal is

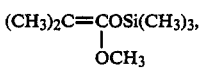

and the phenolic compound is present at a concentration of greater than about 100 parts per million on a molar basis relative to the silyl ketene acetal.

16. A silyl ketene acetal mixture according to claim 15, wherein the phenolic compound is present at a concentration of greater than about than 500 parts per million on a molar basis relative to the silyl ketene acetal.

17. A silyl ketene acetal mixture according to claim 15, wherein the phenolic compound is present at a concentration in the range of about 100 to 10,000 parts per million on a molar basis relative to the silyl ketene acetal.

18. A silyl ketene acetal mixture according to claim 15, wherein the phenolic compound is phenol.

19. A silyl ketene acetal mixture according to claim 15, wherein the phenolic compound is a substituted phenol, said substituted phenol being selected from a group consisting of hydroquinone, 4-methoxyphenol, and 2,6-di-t-butyl-4-methylphenol.

20. A silyl ketene acetal mixture according to claim 1, wherein the silyl ketene acetal is

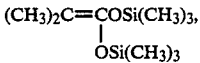

and the phenolic compound is present at a concentration of greater than about 100 parts per million on a molar basis relative to the silyl ketene acetal.

21. A process according to claim 20, wherein the phenolic compound is present at a concentration of greater than about 500 parts per million on a molar basis relative to the silyl ketene acetal.

22. A process according to claim 20, wherein the phenolic compound is present at a concentration of in the range of about 500 to 10,000 parts per million on a molar basis relative to the silyl ketene acetal.

23. A silyl ketene acetal mixture according to claim 20, wherein the phenolic compound is phenol.

24. A silyl ketene acetal mixture according to claim 20, wherein the phenolic compound is a substituted phenol, said substituted phenol being selected from a group consisting of hydroquinone, 4-methoxyphenol, and 2,6-di-t-butyl-4-methylphenol.

* * * * *